(12) United States Patent
Davis et al.

(10) Patent No.: US 10,022,561 B2
(45) Date of Patent: Jul. 17, 2018

(54) RADIOTHERAPEUTIC APPARATUS AND METHOD

(71) Applicant: Elekta Limited, West Sussex (GB)

(72) Inventors: Robert Davis, West Sussex (GB); Peter Davis, West Sussex (GB)

(73) Assignee: Elekta Limited, West Sussex (GB)

( * ) Notice: Subject to any disclaimer, the term of this patent is extended or adjusted under 35 U.S.C. 154(b) by 123 days.

(21) Appl. No.: 15/219,389

(22) Filed: Jul. 26, 2016

(65) Prior Publication Data

US 2017/0028223 A1 Feb. 2, 2017

(30) Foreign Application Priority Data

Jul. 27, 2015 (GB) .................................. 1513195.6

(51) Int. Cl.
*A61N 5/10* (2006.01)

(52) U.S. Cl.
CPC .......... *A61N 5/1048* (2013.01); *A61N 5/1075* (2013.01); *A61N 2005/1074* (2013.01); *A61N 2005/1089* (2013.01)

(58) Field of Classification Search
CPC ................ A61N 5/1048; A61N 5/1075; A61N 2005/1074; A61N 2005/1089
See application file for complete search history.

(56) References Cited

U.S. PATENT DOCUMENTS

| 7,672,428 B1* | 3/2010 | Brown ................. | A61N 5/1048 378/106 |
| 2007/0242705 A1* | 10/2007 | Faure ..................... | H05H 15/00 372/5 |
| 2012/0215051 A1* | 8/2012 | Brown ................. | A61N 5/1042 600/1 |

FOREIGN PATENT DOCUMENTS

| WO | WO 2007/124760 A1 | 4/2006 |
| WO | WO 2011/050887 A1 | 5/2011 |

OTHER PUBLICATIONS

International Search Report for corresponding GB Application No. 1513195.6, filed Jul. 27, 2015.

* cited by examiner

*Primary Examiner* — Mark R Gaworecki
(74) *Attorney, Agent, or Firm* — Finnegan, Henderson, Farabow, Garrett & Dunner LLP

(57) ABSTRACT

A radiotherapy apparatus and method, comprising a source of radiation for delivering pulses of radiation at a base frequency; and a control unit configured to generate a time-averaged power level of x by generating an $n^{th}$ pulse when n is equal to the rounded value of an integer multiple of 1/x, where x is a value between 0 and 1 representing a proportion of a maximum power output of the radiotherapy apparatus. The pulses may form a repeating pulse train pattern, and the control unit may comprise a processing unit configured to provide a pulse train pattern having a number of available slots, the slots being marked as a permitted pulse or a suppressed pulse.

20 Claims, 2 Drawing Sheets

| M | Q | M/Q | \multicolumn{16}{c}{Slot} |
|---|---|-----|---|---|---|---|---|---|---|---|---|---|---|---|---|---|---|---|
|   |   |     | 1 | 2 | 3 | 4 | 5 | 6 | 7 | 8 | 9 | 10 | 11 | 12 | 13 | 14 | 15 | 16 |
| 16 | 1  | 16.00 |   |   |   |   |   |   |   |   |   |    |    |    |    |    |    | 16 |
| 16 | 2  | 8.000 |   |   |   |   |   |   |   | 8 |   |    |    |    |    |    |    | 16 |
| 16 | 3  | 5.333 |   |   |   |   | 5 |   |   |   |   |    | 11 |    |    |    |    | 16 |
| 16 | 4  | 4.000 |   |   |   | 4 |   |   |   | 8 |   |    |    | 12 |    |    |    | 16 |
| 16 | 5  | 3.200 |   |   | 3 |   |   | 6 |   |   |   | 10 |    |    | 13 |    |    | 16 |
| 16 | 6  | 2.667 |   |   | 3 |   | 5 |   |   | 8 |   |    | 11 |    | 13 |    |    | 16 |
| 16 | 7  | 2.286 |   | 2 |   |   | 5 |   | 7 |   | 9 |    | 11 |    |    | 14 |    | 16 |
| 16 | 8  | 2.000 |   | 2 |   | 4 |   | 6 |   | 8 |   | 10 |    | 12 |    | 14 |    | 16 |
| 16 | 9  | 1.778 |   | 2 |   | 4 | 5 |   | 7 |   | 9 | 11 |    | 12 |    | 14 |    | 16 |
| 16 | 10 | 1.600 |   | 2 | 3 |   | 5 | 6 |   | 8 |   | 10 | 11 |    | 13 | 14 |    | 16 |
| 16 | 11 | 1.455 | 1 |   | 3 | 4 |   | 6 | 7 |   | 9 | 10 |    | 12 | 13 |    | 15 | 16 |
| 16 | 12 | 1.333 | 1 |   | 3 | 4 | 5 |   | 7 | 8 | 9 |    | 11 | 12 | 13 |    | 15 | 16 |
| 16 | 13 | 1.231 | 1 | 2 |   | 4 | 5 | 6 | 7 |   | 9 | 10 | 11 | 12 |    | 14 | 15 | 16 |
| 16 | 14 | 1.143 | 1 | 2 | 3 |   | 5 | 6 | 7 | 8 | 9 | 10 | 11 |    | 13 | 14 | 15 | 16 |
| 16 | 15 | 1.067 | 1 | 2 | 3 | 4 | 5 | 6 | 7 |   | 9 | 10 | 11 | 12 | 13 | 14 | 15 | 16 |
| 16 | 16 | 1.000 | 1 | 2 | 3 | 4 | 5 | 6 | 7 | 8 | 9 | 10 | 11 | 12 | 13 | 14 | 15 | 16 |

FIG. 3

RADIOTHERAPEUTIC APPARATUS AND METHOD

CROSS-REFERENCE TO RELATED APPLICATION

This application claims the benefit and priority of prior United Kingdom Patent Application No. GB 1513195.6, filed on Jul. 27, 2015, the entire contents of which are incorporated by reference herein

TECHNICAL FIELD

The present disclosure relates to radiotherapeutic apparatus and a method therefor.

BACKGROUND

A radiotherapy radiation source may be provided by, for example, a radio-frequency (RF) waveguide which may accelerate electrons to a desired energy level, either to subsequently produce x-rays by arranging for the electrons to collide with a tungsten target, for example, or for direct use in electron therapy.

Our WO 2007/124760 describes existing VMAT therapies, in which the dose rate is used as a variable in order to match the maximum speed of the moving machine axes and therefore create the specified dose rate, expressed as mu/mm or mu/°.

Our WO 2011/050887 sets out that a drawback of previously-known VMAT therapies is the longer treatment required because only a limited range of dose rates was available. That document proposed a radiotherapeutic apparatus comprising a source of radiation able to issue pulses of radiation at a base frequency, and a control apparatus arranged to permit or suppress pulses according to a pulse pattern chosen to achieve a selected time-averaged power level, the chosen pulse pattern being one selected from a plurality of pulse patterns, the plurality including at least one pattern consisting of a train of pulses that includes, relative to the base frequency, at least every $n^{th}$ and every $m^{th}$ pulse, where n≠m and the $n^{th}$ and $M^{th}$ pulse are non-coincident.

The pulse pattern generated by that radiotherapeutic apparatus is able to modulate the output dose rate much more precisely than in previous radiotherapeutic apparatus, and thus reduce treatment times.

However, the pulse pattern generated by that invention could, under certain circumstances, include several consecutive permitted pulses followed by several consecutive suppressed pulses. Example pulse train patterns resulting from the apparatus of our '887 are shown in FIG. 1, and that drawing is described in more detail below. In that drawing it can be seen that permitted and suppressed pulses are sometimes grouped into blocks of consecutive permitted pulses and suppressed pulses.

SUMMARY

The efficiency and lifetime of an RF waveguide for radiotherapeutic apparatus can be improved if, for a selected time-averaged power level, permitted and suppressed pulses can be spaced more evenly within a pulse train, thus minimising fluctuation of the electrical power supplied to the waveguide.

The present disclosure therefore provides a radiotherapy apparatus comprising a source of radiation able to issue pulses of radiation at a base frequency, and a control apparatus arranged to achieve a time-averaged power level of x, where x is a value between 0 and 1 representing a proportion of a maximum power output of the apparatus, by permitting an $n^{th}$ pulse if n is equal to the rounded value of (an integer times 1/x).

The rounding operation applied to the integer multiples of 1/x can be a classical rounding to the nearest integer operation, i.e. taking the integer part only of the value after adding one half, or it can be a simpler operation of simply taking the integer part only. In fact, adding a fixed value prior to taking the integer part simply shifts the chosen pulse forward or backward in a sequence and does not significantly affect the overall result, provided that a sufficient number of pulses are issued. For simplicity, therefore, it will usually be easiest simply to take the integer part.

The sequence can be allowed to run indefinitely, or it can be repeated periodically in a pulse train pattern in order to prevent the numbers involved from overflowing. Generally, a longer sequence allows a correspondingly finer level of control over the power level, so a pattern of between $10^1$ and $10^7$ pulses is likely to be sufficient, preferably between $10^2$ and $10^3$ pulses.

Where a pulse train pattern is repeated periodically, a pattern can be derived by defining a number of available slots, M, each slot being capable of being marked as a permitted pulse or a suppressed pulse, the number of permitted and suppressed pulses being selected so that the pattern has a selected number of permitted pulses, Q, the pattern being derived by:
  i) dividing M by Q to calculate a factor P;
  ii) calculating a series of incremented multiples of P, $P_N$=NP, until N=Q, where N increments from one;
  iii) rounding (as above) the values of $P_N$ to produce a set of values $R_N$;
  iv) marking each pulse train pattern slot so that slot positions which correspond to the values of $R_N$ are marked as permitted pulses, and all other slot positions are marked as suppressed pulses.

For a sequence, or a pulse train pattern having particular number of pulse slots, where each permitted pulse results in the emission, from the radiation source, of a particular dose of radiotherapeutic energy (for example x-rays or electrons), and the number of permitted pulses is selected so that over the course of the pulse train a radiation dose is emitted, the permitted pulses are approximately evenly spaced within the sequence or pulse train. The advantage of this approximately even spacing is to minimise fluctuation of the electrical power supplied to a waveguide.

A further advantage of the present disclosure is that it reduces the number of and complexity of calculations required to determine a suitable pulse train, compared with previous techniques. This can either speed up calculations, or enable less complex calculation circuitry to be used.

The control apparatus may store one or more pulse train patterns in a table of a memory. This allows the pulse train pattern(s) to be calculated in advance rather than in real time. After storage, pulse train patterns may be selected without the need to calculate a suitable pulse train pattern each time.

A common form of radiotherapeutic apparatus comprises an RF waveguide and a control apparatus.

The present disclosure also relates to a method of providing pulses to a control apparatus for a radiotherapy apparatus, the radiotherapy apparatus comprising a source of radiation able to issue a sequence of pulses of radiation at a base frequency, and a control apparatus arranged to achieve a time-averaged power level of x, where x is a value between 0 and 1 representing a proportion of a maximum power output of the radiotherapy apparatus, the method comprising permitting an $n^{th}$ pulse if n is equal to the rounded value of (an integer times 1/x).

As above, the rounding operation applied to the integer multiples of 1/x can be a classical rounding to the nearest integer operation, i.e. taking the integer part only of the value after adding one half, or it can be a simpler operation of simply taking the integer part only. In fact, adding a fixed value prior to taking the integer part simply shifts the chosen pulse forward or backward in a sequence and does not affect the overall result, provided that a sufficient number of pulses are issued. For simplicity, therefore, it will usually be easiest simply to take the integer part.

The sequence can be allowed to run indefinitely, or it can be repeated periodically in a pulse train pattern in order to prevent the numbers involved from overflowing. Generally, a longer pattern allows a correspondingly finer level of control over the power level, so a pattern of between $10^1$ and $10^7$ pulses is likely to be sufficient, preferably between $10^2$ and $10^3$ pulses.

Where a pulse train pattern is repeated periodically, a pattern can be derived by defining a number of available slots, M, each slot being capable of being marked as a permitted pulse or a suppressed pulse, the number of permitted and suppressed pulses being selected so that the pattern has a selected number of permitted pulses, Q, the method comprising the steps of:
 i) dividing M by Q to calculate a factor P;
 ii) calculating a series of incremented multiples of P, $P_N$=NP, until N=Q, where N increments from one;
 iii) rounding (as above) the values of $P_N$ to produce a set of values $R_N$;
 iv) marking each pulse train pattern slot so that slot positions which correspond to the values of $R_N$ are marked as permitted pulses, and all other slot positions are marked as suppressed pulses, so that a pulse train pattern is generated.

The method may further comprise the step of generating a series of radiotherapeutic doses to a patient, each dose being generated according to the pulse train pattern.

The control apparatus may store one or more pulse train patterns in a table of a memory. This allows the pulse train pattern(s) to be calculated in advance rather than in real time. After storage, pulse train patterns may be selected without the need to derive a suitable pulse train pattern each time.

Radiotherapeutic apparatus may operate in an "open loop" or a "closed loop" arrangement. In an open loop arrangement, a dose provided by a pulse provided by a radiation source is known, to a degree of precision, and thus the number or rate of pulses to be provided to produce a desired dose rate can be calculated. There is some variability in the dose per pulse generated, however. Thus, in an open loop arrangement there is a degree of uncertainty in the actual dose rate being provided to a patient.

In a closed loop arrangement, the dose rate being provided is measured, so that the output from the radiotherapeutic apparatus can be calibrated. The calibration steps may be as follows: selecting a dose rate corresponding to a desired dose rate, generating a pulse rate pattern corresponding to the selected dose rate, applying the pulse rate pattern to the control apparatus and thus to the radiotherapeutic apparatus, measuring the actual dose rate generated, and varying the selected dose rate, if necessary, to increase or decrease the actual dose rate generated. The actual dose rate generated may be measured by using an ion chamber beneath an x-ray target, for example.

A feedback mechanism may be provided, to compare the actual dose rate generated with the selected dose rate. A dose rate may be described in terms of monitor units per unit time.

Thus, the method of the present disclosure may further comprise the steps of:
 measuring an output from the radiation source; comparing the output with a desired output; and using the result of the comparison between the measured output and the desired output to vary the selected number of permitted pulses, Q.

Similarly, the apparatus of the present disclosure may further comprise a unit for comparing an output of the radiation source with a desired output.

BRIEF DESCRIPTION OF THE DRAWINGS

An embodiment of the present disclosure will now be described by way of example, with reference to the accompanying figures in which:
FIG. 3 is a table showing a worked example of the possible pulse train patterns in a situation where a certain number of slots are available.

DETAILED DESCRIPTION

Figure 1:
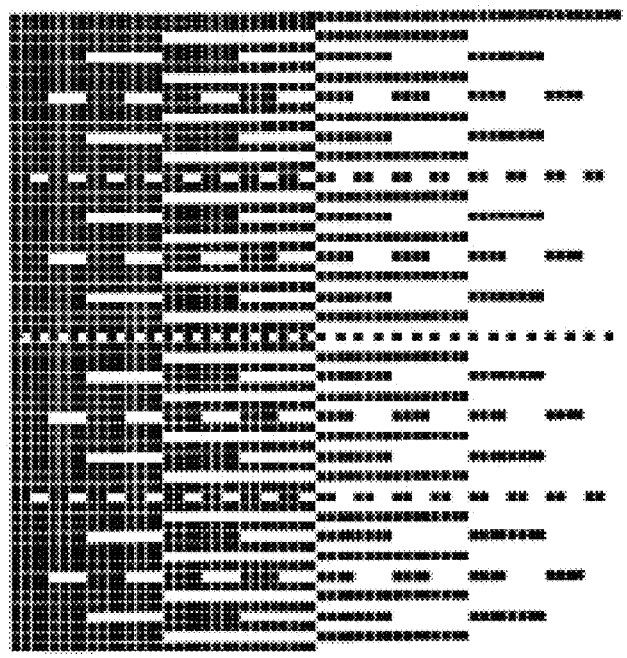
FIG. 1 is a graphical representation of a known set of pulse train patterns.

In FIG. 1 a graphical representation of a known set of pulse train patterns is set out as a series of "pixels", so that a dark pixel represents a permitted pulse, and a light pixel represents a suppressed pulse. Along the horizontal axis, from left to right, are decreasing selected numbers of permitted pulses. The vertical axis represents possible pulse slots. In this way, in the leftmost vertical column, all pixels are dark, representing that each possible pulse slot is marked as permitted. In the rightmost vertical column, nearly all the pixels are light, representing that nearly all possible pulse slots are marked as suppressed.

Figure 2:
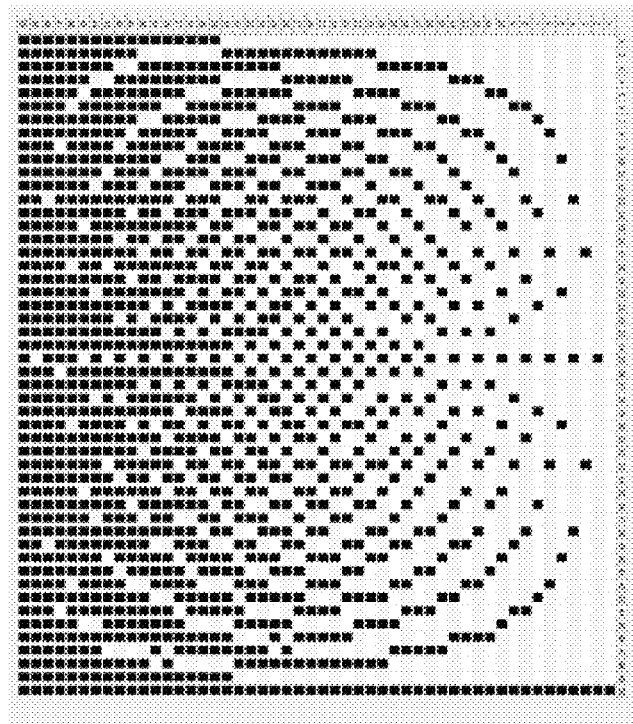
FIG. 2 is a graphical representation of a set of pulse train patterns embodying the present disclosure.

FIG. 2 is a graphical representation, in a similar style to that of FIG. 1. However, in FIG. 2 the distribution of permitted and suppressed pulses, as represented by dark and light pixels, is according to the method and apparatus of the present disclosure. Thus, in the leftmost and rightmost columns of FIG. 2, the arrangement of pixels (and thus pulses) is similar, because there are so few suppressed and permitted pulses in the relevant pulse train pattern, respectively. However, in the situation towards the central section of the horizontal axis, in which a mixture of permitted and suppressed pulses is found within a pulse train pattern, it can be seen that the dark and light pixels (and thus the permitted and suppressed pulses) are substantially evenly spaced within the pulse train pattern.

The method by which these pulse train patterns are generated is as referenced above. In other words, after defining a number of available slots, M, with each slot being capable of being marked as a permitted pulse or a suppressed pulse, and choosing a number of permitted and suppressed pulses so that the pattern has a selected number of permitted pulses, Q, which generates the required power level, the method then calls for the control unit to:
 v) divide M by Q to calculate a factor P;
 vi) calculate a series of incremented multiples of P, $P_N$=NP, until N=Q, where N increments from one;

vii) round the values of $P_N$ to produce a set of values $R_N$;
viii) mark each pulse train pattern slot so that slot positions which correspond to the values of $R_N$ are marked as permitted pulses, and all other slot positions are marked as suppressed pulses, so that a pulse train pattern is generated.

This then produces a pulse train pattern such as that shown in FIG. 2, which can be repeated at will. A small amount of mathematical manipulation shows that this is equivalent to permitting an $n^{th}$ pulse if n is equal to the rounded value of (an integer times 1/x), where x is a value between 0 and 1 representing a proportion of a maximum power output of the radiotherapy apparatus, thus achieving a time-averaged power level of x of the maximum.

Examples of steps as set out above for given values of M and Q now follow.

EXAMPLE 1

M=16, Q=8

| P = M/Q = 2 | | | | |
|---|---|---|---|---|
| $P_1$ = | 2 | $R_1$ = | 2.5 | $R_1$(truncated) = | 2 |
| $P_2$ = | 4 | $R_2$ = | 4.5 | $R_2$(truncated) = | 4 |
| $P_3$ = | 6 | $R_3$ = | 6.5 | $R_3$(truncated) = | 6 |
| $P_4$ = | 8 | $R_4$ = | 8.5 | $R_4$(truncated) = | 8 |
| $P_5$ = | 10 | $R_5$ = | 10.5 | $R_5$(truncated) = | 10 |
| $P_6$ = | 12 | $R_6$ = | 12.5 | $R_6$(truncated) = | 12 |
| $P_7$ = | 14 | $R_7$ = | 14.5 | $R_7$(truncated) = | 14 |
| $P_8$ = | 16 | $R_8$ = | 16.5 | $R_8$(truncated) = | 16 |

Thus, pulse slots 2, 4, 6, 8, 10, 12, 14, and 16 are marked as permitted pulses, and the remaining pulse slots are marked as suppressed pulses. As a result, 8 pulses are issued out of every 16 slots, and the pulses are evenly spaced.

EXAMPLE 2

M=32, Q=7

| P = M/Q = 4.5714 | | | | |
|---|---|---|---|---|
| $P_1$ = | 4.5714 | $R_1$ = | 5.0714 | $R_1$(truncated) = | 5 |
| $P_2$ = | 9.1428 | $R_2$ = | 9.6428 | $R_2$(truncated) = | 9 |
| $P_3$ = | 13.7142 | $R_3$ = | 14.2142 | $R_3$(truncated) = | 14 |
| $P_4$ = | 18.2856 | $R_4$ = | 18.7856 | $R_4$(truncated) = | 18 |
| $P_5$ = | 22.857 | $R_5$ = | 23.357 | $R_5$(truncated) = | 23 |
| $P_6$ = | 27.4284 | $R_6$ = | 27.9284 | $R_6$(truncated) = | 27 |
| $P_7$ = | 31.9998 | $R_7$ = | 32.4998 | $R_7$(truncated) = | 32 |

Thus, pulse slots 5, 9, 14, 18, 23, 27, and 32 are marked as permitted pulses, and the remaining pulse slots are marked as suppressed pulses. A total of 7 pulses are issued out of every 32 slots, and (again) the pulses are relatively evenly spaced with the gap varying by only ±1 slot.

The spacing of the permitted pulses within the resulting pulse train pattern in each of the above examples is approximately even. In Example 1, the permitted pulses are all spaced apart by one suppressed pulse, and in Example 2, the permitted pulses are spaced apart by four to five suppressed pulses.

The skilled reader will appreciate that these are examples only, and many other possibilities exist, where different values of M and Q are selected.

FIG. 3 is a table showing a worked example of a pulse train with 16 possible slots. Thus, M=16, as shown in the leftmost column of the table. The next column to the right shows incrementing values of Q, from 1 in the first row next to the uppermost M value, incrementing in each row downwards, reaching 16 in the lowermost row of the table. The next column to the right after that shows the value of P, namely M divided by Q (P=M/Q). The value of P determines which pulse train pattern slots are marked as permitted, and which are marked as suppressed. In the table, pulse slot positions are numbered in the row above the first row of the worked example, i.e. incrementally from 1 to 16. Where the method and apparatus of the present disclosure would mark a slot as permitted, the slot number appears in the relevant column for that slot. For example, where M=16 and Q=1, only slot 16 is marked as permitted, and thus in the table the number 16 appears in that column of that row. Where M=16 and Q=16, every slot is marked as permitted, and so every slot value appears in its column of that row. It can be seen from the table of FIG. 3 that the permitted and unpermitted slots follow a similar pattern to that of the dark and light pixels of FIG. 2, although it will be appreciated that the table of FIG. 3 is calculated with different boundary conditions, i.e. selected values of M.

It will of course be understood that many variations may be made to the above-described embodiments without departing from the scope of the present disclosure. For example, values of M and Q may be selected from a very wide range depending on the characteristics of the radiation source being used, and also the skilled person would appreciate that certain steps could be replaced which are logically similar or identical to those set out, but which at first glance appear different. Furthermore, other closed loop feedback arrangements will occur to the skilled reader.

The invention claimed is:

1. A radiotherapy apparatus comprising:
    a source of radiation for delivering pulses of radiation at a base frequency; and
    a control unit configured to generate a time-averaged power output level of x by generating an $n^{th}$ pulse when n is equal to the rounded value of an integer multiple of 1/x, where x is a value between 0 and 1 representing a proportion of a maximum power output level of the radiotherapy apparatus.

2. The apparatus according to claim 1, wherein the pulses form a repeating pulse train pattern.

3. The apparatus according to claim 2, wherein the control unit comprises a processing unit configured to provide a pulse train pattern having a number of available slots M, the slots being marked as a permitted pulse or a suppressed pulse, the processing unit being further configured to generate the pulse train pattern with a selected number of permitted pulses, Q, by:
    dividing M by Q to calculate a factor P;
    calculating a series of incremented multiples of P, $P_N$=NP, until N=Q, where N increments from one;
    rounding the values of $P_N$ to produce a set of values $R_N$; and
    marking the slots so that positions of the slots corresponding to the values of $R_N$ are marked as permitted pulses, and all other slot positions are marked as suppressed pulses.

4. The apparatus according to claim 3, wherein the pulse train pattern has between $10^1$ and $10^7$ slots.

5. The apparatus according to claim 3, wherein the pulse train pattern has between $10^2$ and $10^3$ slots.

6. The apparatus according to claim 2, wherein the control unit comprises a memory for storing one or more pulse train patterns in a table.

7. The apparatus according to claim 1, further comprising:
a measuring unit for measuring a radiation dose rate generated by the radiotherapeutic apparatus; and
a calibration unit for varying the power output level to modify the generated dose rate to match a selected dose rate.

8. The apparatus according to claim 1, further comprising:
a linear accelerator fed by the source of radiation.

9. A method of providing pulses to a control unit of a radiotherapy apparatus, the radiotherapy apparatus comprising a source of radiation for delivering a sequence of pulses of radiation at a base frequency, the method comprising:
generating, by the control unit a time-averaged power output level of x; and
generating an $n^{th}$ pulse when n is equal to the rounded value of an integer multiple of 1/x, where x is a value between 0 and 1 representing a proportion of a maximum power output level of the radiotherapy apparatus.

10. The method according to claim 9, wherein the pulses form a repeating pulse train pattern.

11. The method according to claim 10, wherein:
the pulse train pattern has a number of available slots M, the slots being marked as a permitted pulse or a suppressed pulse; and
the control unit is configured to generate the pulse train pattern with a selected number of permitted pulses Q, the method further comprising the steps of:
dividing M by Q to calculate a factor P;
calculating a series of incremented multiples of P, $P_N$=NP, until N=Q, where N increments from one;
rounding the values of $P_N$ to produce a set of values $R_N$; and
marking the slots so that positions of the slots corresponding to the values of $R_N$ are marked as permitted pulses, and all other slot positions are marked as suppressed pulses.

12. The method according to claim 11, wherein the pulse train pattern has between $10^1$ and $10^7$ slots.

13. The method according to claim 11, wherein the pulse train pattern has between $10^2$ and $10^3$ slots.

14. The method according to claim 11, further comprising the steps of:
measuring a radiation dose rate generated by the radiotherapeutic apparatus; and
varying the power output level to modify the generated dose rate to match a selected dose rate.

15. The method according to claim 10, wherein the control unit comprises a memory for storing one or more pulse train patterns in a table.

16. A radiotherapeutic apparatus comprising:
a source of radiation for delivering pulses of radiation at a base frequency;
a linear accelerator fed by the radiation source; and
a control unit configured to generate a time-averaged power output level of x by generating an $n^{th}$ pulse when n is equal to the rounded value of an integer multiple of 1/x, where x is a value between 0 and 1 representing a proportion of a maximum power output level of the radiotherapy apparatus.

17. The apparatus according to claim 16, wherein the pulses form a repeating pulse train pattern.

18. The apparatus according to claim 17, wherein the control unit comprises a processing unit configured to provide a pulse train pattern having a number of available slots M, the slots being marked as a permitted pulse or a suppressed pulse, the processing unit being further configured to generate the pulse train pattern with a selected number of permitted pulses, Q, by:
dividing M by Q to calculate a factor P;
calculating a series of incremented multiples of P, $P_N$=NP, until N=Q, where N increments from one;
rounding the values of $P_N$ to produce a set of values $R_N$; and
marking the slots so that positions of the slots corresponding to the values of $R_N$ are marked as permitted pulses, and all other slot positions are marked as suppressed pulses.

19. The apparatus according to claim 18, wherein the pulse train pattern has between $10^2$ and $10^3$ slots.

20. The apparatus according to claim 16, further comprising:
a measuring unit for measuring a radiation dose rate generated by the radiotherapeutic apparatus; and
a calibration unit for varying the power output level to modify the generated dose rate to match a selected dose rate.

* * * * *